US00PP12735P2

(12) United States Plant Patent
Janssen

(10) Patent No.: US PP12,735 P2
(45) Date of Patent: Jun. 25, 2002

(54) BEAUCARNEA PLANT NAMED 'FACH9901BEAU'

(76) Inventor: Cornelis Johannes Janssen, Harteveldlaan 10, 2675 LE Honselersdijk (NL)

( * ) Notice: Subject to any disclaimer, the term of this patent is extended or adjusted under 35 U.S.C. 154(b) by 6 days.

(21) Appl. No.: 09/797,252

(22) Filed: Mar. 1, 2001

(51) Int. Cl.[7] ..... A01H 5/00
(52) U.S. Cl. ..... Plt./373
(58) Field of Search ..... Plt./373

(56) References Cited

PUBLICATIONS

UPOV–ROM GTITM Computer Database 2001/01, Feb. 6, 2001, GTI Jouve Retrieval Software, Citation for 'Fach9901beau'.*

* cited by examiner

*Primary Examiner*—Bruce R. Campell
*Assistant Examiner*—Annette Para

(57) ABSTRACT

A distinct cultivar of Beaucarnea plant named 'FACH9901BEAU', upright growth habit; dark green and light yellow variegated leaves that are outwardly arching; and excellent post-production longevity.

1 Drawing Sheet

BACKGROUND OF THE INVENTION

The present invention relates to a new and distinct cultivar of Beaucarnea plant, botanically known as *Beaucarnea recurvata*, and hereinafter referred to by the name 'FACH9901BEAU'.

The new cultivar was discovered by the Inventor in a greenhouse in Honselersdijk, The Netherlands as a naturally-occurring whole plant mutation of an unidentified selection of *Beaucarnea recurvata*. The new Beaucarnea was observed as a single plant in a group of plants of the parent selection in 1996. This plant was selected on its unique leaf variegation pattern as plants of the parent selection do not have variegated leaves.

Asexual propagation of the new cultivar at Honselersdijk, The Netherlands, by tissue culture has shown that the unique features of this new Beaucarnea plant are stable and reproduced true to type in successive generations of asexual propagation.

SUMMARY OF THE INVENTION

The new Beaucarnea has not been observed under all possible environmental conditions. The phenotype may vary somewhat with variations in environment such as temperature and light intensity, without, however, any variance in genotype.

The following traits have been repeatedly observed and are determined to be the unique characteristics of 'FACH9901BEAU'. These characteristics in combination distinguish 'FACH9901BEAU' as a new and distinct cultivar:

1. Upright growth habit.
2. Dark green and light yellow variegated leaves that are outwardly arching.
3. Excellent post-production longevity.

Plants of the new Beaucarnea differ from plants of the parent selection primarily in leaf coloration; in addition, leaves of plants of the new Beaucarnea are more uniform in shape and size than leaves of plants of the parent selection.

DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Beaucarnea. The photograph comprises a top perspective view of a typical potted plant of the parent selection (left) and a typical potted plant of 'FACH9901BEAU' (right) showing the difference in the leaf coloration.

DETAILED BOTANICAL DESCRIPTION

The following observations, measurements and comparisons describe plants grown in Honselersdijk, The Netherlands, in a glass-covered greenhouse with day temperatures about 20 to 26° C. and night temperatures about 20 to 23° C. Plants were about 1.5 years from planting and were grown in 19-cm containers. In this description, color references are made to The Royal Horticultural Society Colour Chart except where general terms of ordinary dictionary significance are used.

Botanical classification: *Beaucarnea recurvata* cultivar FACH9901BEAU.

Parentage: Naturally-occurring whole plant mutation of an unidentified selection of *Beaucarnea recurvata*, not patented.

Propagation:

*Method.*—By tissue culture.

*Time to initiate roots on a tissue-cultured plantlet.*—About 70 to 84 days at 23 to 24° C.

*Time to produce a root tissue-cultured plant.*—About 120 to 150 days at 23 to 24° C.

*Root description.*—Fine.

Plant description:

*Plant shape.*—Upright plant habit with outwardly arching leaves; symmetrical; vigorous growth habit.

*Usage.*—Appropriate for 19-cm containers; indoor plant.

*Plant height from soil level to top of leaf plane.*—About 25 cm.

*Plant diameter or spread.*—About 75 cm.

*Foliage description.*—Arrangement: Single; rosette. Length: About 65 cm. Width: About 1.2 to 1.4 cm. Shape: Linear. Apex: Acute. Attachment: Decurrent. Margin: Entire with very fine serrations, scaberulous. Aspect: Initially upright, then outwardly arching. Texture: Leathery, smooth, glabrous. Venation pattern: Parallel. Color: Longitudinally variegated. Marginal areas are light yellow and the central area is dark green. On the largest leaves, the marginal areas are each about 3 mm wide and the central area is about 8 mm wide. Young leaves, upper and lower surfaces: Central area: At base, 144A; mid-section and apex, 147A. Marginal areas: 2C. Expanded leaves, upper and lower surfaces: Central area: 147A. Marginal areas: 2C.

Flower description: Flowers have not been observed on plants of the new Beaucarnea.

Disease resistance: Plants of the new Beaucarnea have not been observed to be resistant to pathogens common to Beaucarnea.

Postproduction longevity: Plants of the new Beaucarnea have been observed to maintain good leaf substance for more than two years in an interior environment.

Weather tolerance: Plants of the new Beaucarnea have been observed to be tolerant to temperatures ranging from 10 to at least 40° C.

It is claimed:

1. A new and distinct cultivar of Beaucarnea plant named 'FACH9901BEAU' as illustrated and described.

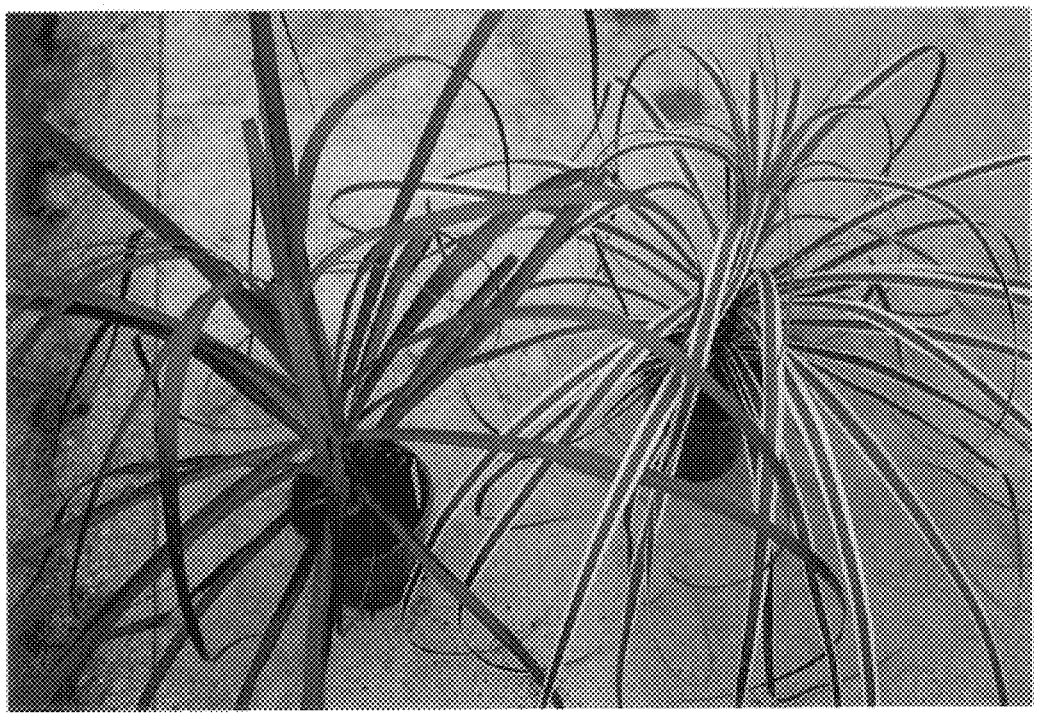

* * * * *